US012642566B2

(12) United States Patent
Kent

(10) Patent No.: US 12,642,566 B2
(45) Date of Patent: Jun. 2, 2026

(54) DEVICES AND METHODS FOR LATERAL FIXATION SYNDESMOSIS REPAIR

(71) Applicant: DePuy Synthes Products, Inc., Raynham, MA (US)

(72) Inventor: Todd J. Kent, Philadelphia, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 392 days.

(21) Appl. No.: 17/983,488

(22) Filed: Nov. 9, 2022

(65) Prior Publication Data

US 2024/0148421 A1    May 9, 2024

(51) Int. Cl.
  *A61B 17/84* (2006.01)
  *A61B 17/68* (2006.01)

(52) U.S. Cl.
  CPC ...... *A61B 17/846* (2013.01); *A61B 2017/681* (2013.01)

(58) Field of Classification Search
  CPC ..... A61B 17/72; A61B 17/7241; A61B 17/68; A61B 17/683; A61B 17/04; A61B 17/0401; A61B 17/84; A61B 17/846
  See application file for complete search history.

(56) References Cited

U.S. PATENT DOCUMENTS

| 5,248,313 | A | 9/1993 | Greene et al. | |
| 5,306,290 | A | 4/1994 | Martins et al. | |
| 7,963,966 | B2 * | 6/2011 | Cole ................... | A61B 17/725 606/62 |
| 8,888,779 | B2 | 11/2014 | Senn et al. | |
| 9,277,912 | B2 * | 3/2016 | Donate .............. | A61B 17/0401 |
| 9,421,049 | B2 | 8/2016 | Rogachefsky | |
| 9,737,347 | B2 | 8/2017 | Schlienger et al. | |
| 9,826,969 | B2 | 11/2017 | Larsen | |
| 10,327,826 | B2 | 6/2019 | Horrell et al. | |
| 10,492,774 | B2 | 12/2019 | Larsen | |
| 10,722,229 | B2 | 7/2020 | O'Donnil et al. | |
| 11,253,301 | B2 | 2/2022 | Larsen et al. | |
| 2002/0198527 | A1 | 12/2002 | Muckter | |
| 2006/0264944 | A1 | 11/2006 | Cole et al. | |
| 2012/0172936 | A1 * | 7/2012 | Horrell .............. | A61B 17/0401 606/104 |
| 2016/0038186 | A1 | 2/2016 | Herzog et al. | |
| 2016/0287302 | A1 * | 10/2016 | Horrell ................. | A61B 17/84 |
| 2017/0258572 | A1 * | 9/2017 | Gordon .............. | A61B 17/1782 |
| 2018/0049784 | A1 | 2/2018 | Gault et al. | |
| 2019/0223925 | A1 * | 7/2019 | Miyahara .............. | A61B 17/72 |
| 2020/0022730 | A1 * | 1/2020 | Manitzaris ........... | A61B 17/683 |
| 2020/0405329 | A1 * | 12/2020 | Liu .................... | A61B 17/8886 |

FOREIGN PATENT DOCUMENTS

| CN | 108186096 A | 6/2018 |
| EP | 3 206 607 B1 | 5/2018 |
| RU | 2461366 C1 | 9/2012 |

OTHER PUBLICATIONS

International Search Report and Written Opinion dated Jan. 24, 2024, from corresponding International Application No. PCT/IB2023/060939.

* cited by examiner

*Primary Examiner* — Christopher J Beccia

(57) ABSTRACT

An example apparatus is provided for placing a nail and a first anchor within a first bone, such as the fibula. The first anchor may include a proximal end and a distal end and may be configured for insertion into a first hole in the first bone, wherein the proximal end may be configured to interface with the nail.

19 Claims, 14 Drawing Sheets

DEVICES AND METHODS FOR LATERAL FIXATION SYNDESMOSIS REPAIR

FIELD

The present invention generally relates to devices and methods for syndesmosis repair via lateral fixation. More specifically, certain embodiments relate to systems and methods for fixation of the distal tibia and distal fibula following an injury to the corresponding syndesmotic joint.

BACKGROUND

A syndesmotic injury results when a traumatic injury damages the ligaments that span the gap between the distal tibia and fibula. This can be the result of a high ankle sprain, with no fracture of the fibula, or can also accompany a fibular fracture in a Weber B or Weber C fracture.

A surgeon can determine the presence of a syndesmotic injury by direct visualization of the joint or through radio-graphic imaging while positioning the ankle in a mortise view orientation. In either case, loads are applied to the joint in either a direct lateral load applied to the fibula or by applying an external rotation load to the foot. While the load is being applied, the relative distance between the fibula and the tibia, the fibula and the talus, and the tibia and the talus are observed to determine the level of damage sustained by the ligaments that typically hold the syndesmotic joint together.

If a syndesmotic injury is found to be present, the typical treatment involves stabilizing the fibula and tibia with respect to each other in the proper orientation and holding them there throughout the soft tissue healing period to allow the ligaments to re-attach and heal. In the event of a syndesmotic injury with a corresponding fibula fracture, this is done while also stabilizing the fibular fracture, which is usually accomplished with a small fracture plate on the lateral side of the fibula. Traditionally the method of stabi-lization has been to place one or more cortical screws across the syndesmosis, with the head against the lateral face of the fibula and the tip of the screw being in the middle of the tibia or in the medial cortex of the tibia.

This form of treatment, whereby the lateral aspect of the syndesmotic fixation sits on the lateral face of the bone, can result in unstable ankle fractures as any weight or force provided by the lateral aspect can be transferred through the fibular fracture itself. Additionally, any retained hardware under a lateral malleolar incision may cause irritation and discomfort to the skin and soft tissue.

Accordingly, alternative apparatus and methods for pro-viding lateral fixation syndesmosis repair of the distal tibia and fibula following a syndesmotic injury would be useful.

SUMMARY

The present invention is directed to apparatus and meth-ods for stabilizing a joint between two bones, e.g., the tibia and fibula, during the soft tissue healing period following a traumatic injury.

In an exemplary application, the apparatus and methods herein may be configured to provide substantially rigid tensile fixation between the tibia and fibula while allowing the small amount of shear and rotational motion required for a standard gait. This may make it possible for patients to return to weight-bearing earlier, which may improve clinical outcomes, and/or may also reduce the number of follow-up hardware-removal surgeries.

An example apparatus is provided for placing a nail and a first anchor within a first bone, such as the fibula. The first anchor may include a proximal end and a distal end, and may be configured for insertion into a first hole in the first bone, wherein the proximal end may be configured to interface with the nail.

The proximal end of the first anchor may be configured to lay flush and/or countersunk to the first bone.

The apparatus may further include a second anchor con-figured to fixate to a second bone, such as the tibia, and a flexible segment extending between the first and second anchors and configured to adjust a distance between the first and second bones.

The second anchor may include a proximal end and a distal end configured for insertion into a second hole in the second bone. The second anchor may pass through the first hole and be inserted within the second bone in the second hole from its distal end to its proximal end. The second hole may be disposed on a first side of the second bone, and the second anchor may be configured such that there is a distance between the distal end of the second anchor and a second side of the second bone.

The flexible segment may extend at least one of between or beyond the distal end of the second anchor and the proximal end of the first anchor.

The second anchor may include a button configured to engage with a second side of the second bone and to receive a distal end of the flexible segment.

The first anchor may include at least one opening con-figured to receive one or more proximal ends of the flexible segment. The flexible segment may be configured to adjust the distance between the first and second bones when the proximal ends are pulled in a proximal direction through the at least one opening.

The nail may include a bore hole, and the first anchor may be configured for insertion into the bore hole. The bore hole may be a non-threaded bore hole.

The apparatus may further include a cap configured to engage with the proximal end of the first anchor.

The apparatus may further include a sleeve configured for insertion into the bore hole of the nail, wherein the first anchor is configured for insertion into the sleeve.

An example method is provided for fixating a nail within a first bone, for example, a fibula, and fixating a first anchor to the first bone. The first anchor may include a proximal end and a distal end. The first anchor may be configured for insertion into a first hole in the first bone. The proximal end of the first anchor may be configured to interface with the nail.

The method may further provide for fixating a second anchor to a second bone, for example, a tibia, and fixating a flexible segment between the first and second anchors. The flexible segment may be configured to adjust a distance between the first and second bones.

The proximal end of the first anchor may be configured to lay flush and/or countersunk to the first one.

The nail may include a non-threaded bore hole.

The method may further include inserting a sleeve into the non-threaded bore hole of the nail. Fixating the first anchor to the first bone may include inserting the distal end of the first anchor into the non-threaded bore hole of the nail and into the sleeve.

The method may further include fixating a cap to the proximal end of the first anchor.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

The example devices and methods of treatment described herein generally involve providing syndesmosis repair of two bones, such as the tibia and fibula bones, via lateral fixation in the fibula bone. That is, a support, such as a nail, may be implanted in the fibula bone such that an apparatus used for the approximation of the fibula and tibia may engage with the nail rather than the lateral side or face of the fibula bone. This configuration may help to prevent an unstable fibular fracture, and/or decrease patient recovery time associated with a fibular fracture, as any weight or force placed on the syndesmotic injury during recovery (e.g., via movement) may be transferred through the nail as opposed to the fibular fracture itself.

Various example systems and methods are presented herein. Features from each example are combinable with other examples as understood by persons skilled in the pertinent art.

Figure 1:
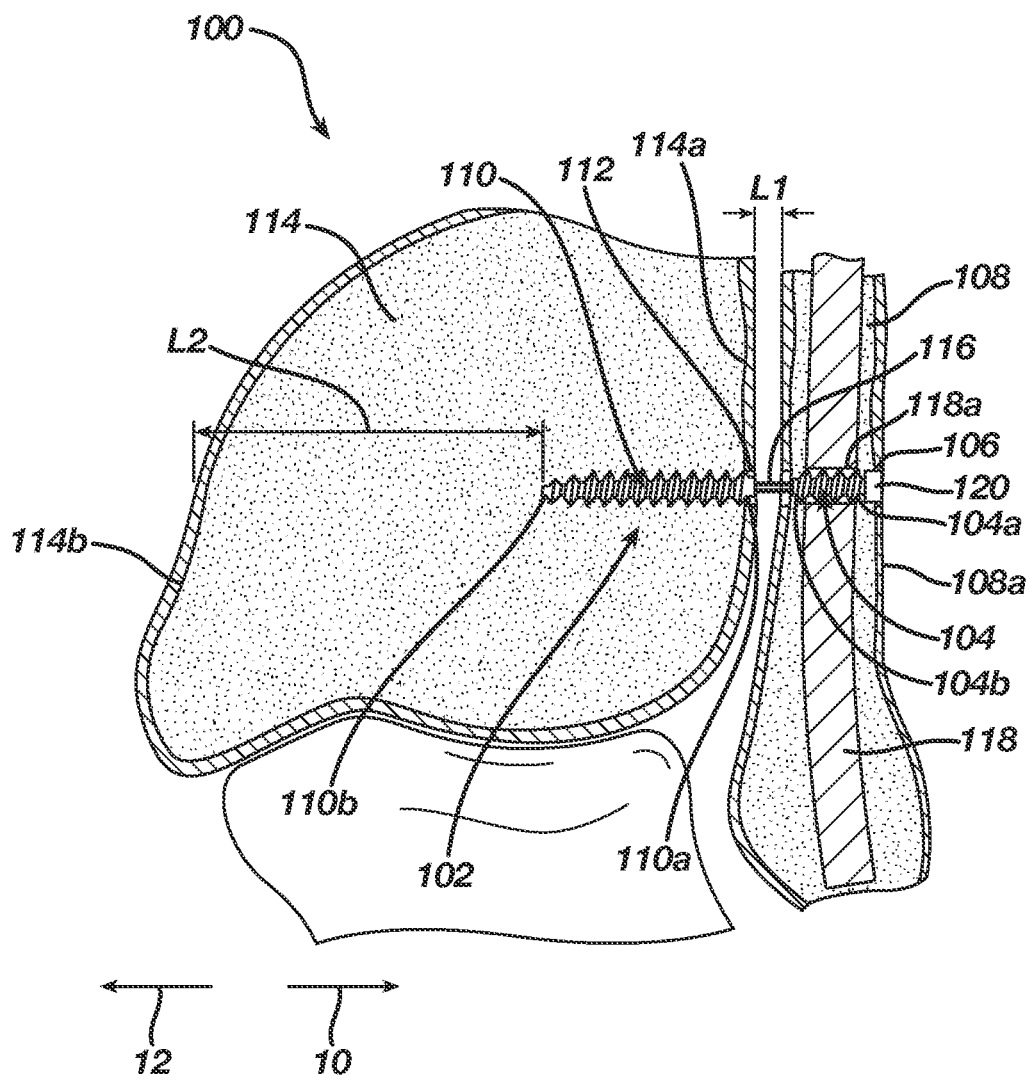
FIG. 1 is an illustration of an example system for lateral fixation syndesmosis repair according to aspects of the present invention.

FIG. 1 is an illustration of an example system 100 for lateral fixation syndesmosis repair. The system 100 may include an apparatus 102 for the approximation of two bones, such as the tibia and fibula bones. The apparatus 102 may include a first anchor 104, which may include a proximal end 104a and a distal end 104b configured for insertion into a first hole 106 in a first bone 108, e.g., a fibula bone. The apparatus 102 may further include a second anchor 110, which may include a proximal end 110a and a distal end 110b configured for insertion into a second hole 112 in a second bone 114, e.g., a tibia bone. The apparatus 102 may further include a flexible segment 116 extending between the first anchor 104 and the second anchor 110. The flexible segment 116 may be configured to adjust a distance L1 between the first and second bones 108, 114.

Figure 6:
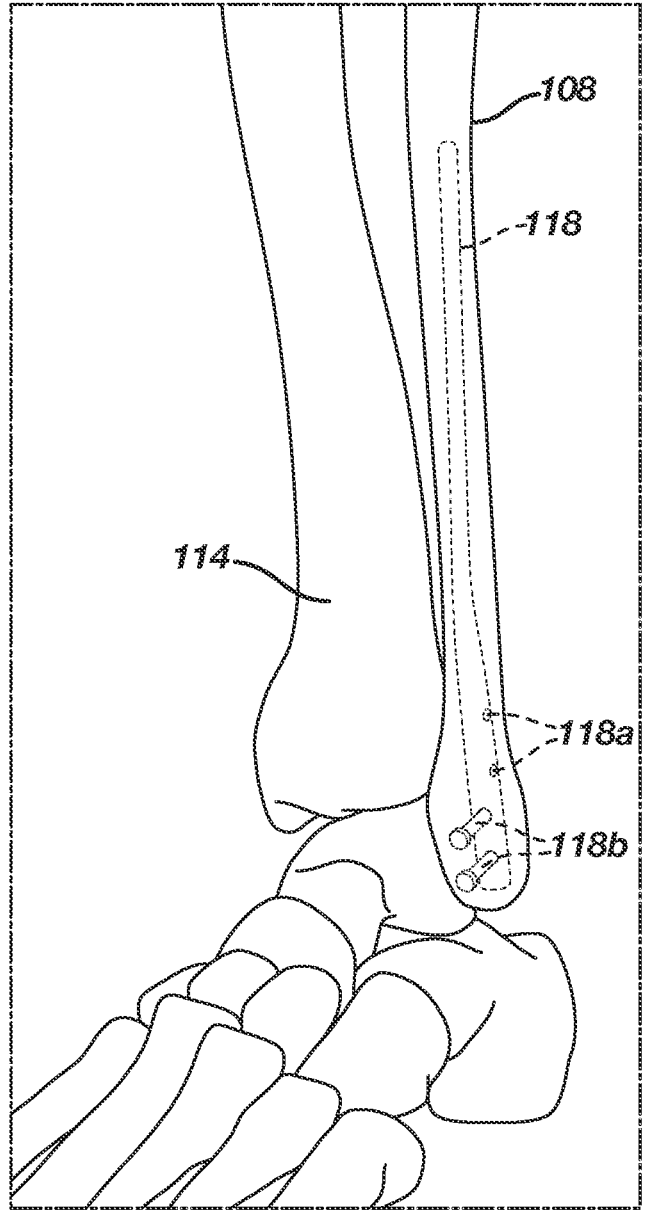
FIG. 6 is an illustration of an element of a system for lateral fixation syndesmosis repair according to aspects of the present invention.

The apparatus 102 may further include a nail 118 disposed within the first bone 108. For example, the nail 118 may be disposed approximately vertically within the first bone 108, and fastened to the first bone 108 via one or more nail fasteners 118b (FIG. 6). The nail 118 may include one or more bore holes 118a, such that the first anchor 104 may be inserted into and/or through the bore hole(s) 118a, and/or the second anchor 110 may be inserted through the bore hole(s) 118a (e.g., prior to being inserted into the second bone 114), as further discussed below. In some embodiments, the proximal end 104a of the first anchor 104 may be configured to interface with the nail 118. For example, once inserted into a bore hole 118a of nail 118, the proximal end 104a of the first anchor 104 may be configured to lay flush and/or countersunk to the first bone 108. A benefit of such configuration is that the first anchor 104 can engage with the nail 118 rather than the lateral side of the first bone 108, which may help to prevent an unstable fibular fracture, and/or to decrease patient recovery time associated with a fibular fracture, as discussed above.

The bore hole(s) 118a of nail 118 may be threaded or non-threaded. When bore hole(s) 118a are threaded, first anchor 104 may directly interface with the bore hole(s) 118a. For example, first anchor 104, having external threads 204 (as further discussed below with respect to FIG. 2A), can be screwed directly into a threaded bore hole 118(a). Alternatively, when bore hole(s) 118a are non-threaded, apparatus 102 may further include one or more additional components to provide engagement between the first anchor 104 and the bore hole(s) 118a. For example, apparatus 102 may further include a cap 120 configured to engage with the proximal end 104a of the first anchor 104. As particularly shown in FIG. 1, cap 120 may be configured to sit flush and/or countersunk to the lateral side of the first bone 108, and may engage with the proximal end 104a of first anchor 104 to prevent first anchor 104 from slipping distally through a non-threaded bore hole 118a. As another example, apparatus 102 may include a sleeve 124 configured for insertion into a non-threaded bore hole 118a, as further discussed below with respect to FIG. 5.

The first and/or second anchors 104, 110 can include any type of suture anchor, and can be manufactured from a surgical stainless steel or other suitable biocompatible material, such as 316 LVM stainless steel, titanium, and other suitable materials, such as nitinol, bio-absorbables, or non-absorbables (e.g., PEEK). First and/or second anchors 104, 110 can also include an "all-textile" anchor (e.g., VERSA-LOOP™).

The second anchor 110 can pass through the first hole 106 in the first bone 108, and in such embodiment including nail 118, through the bore hole(s) 118a of nail 118. Second anchor 110 can also pass through the second hole 112 in the second bone 114 to be inserted (e.g., screwed, threaded, or pushed) within the second bone 114 in the second hole 112. The second anchor 110 can be inserted into the second bone 114 from its distal end 110b to its proximal end 110a such that the second anchor 110 does not extend all the way through the second bone 110. That is, the second hole 112 may be disposed on a first side 114a (e.g., the lateral or proximal 10 side) of the second bone 114, and the second anchor 110 may be configured such that a distance L2 remains between the distal end 110b of the second anchor 110 and a second side 114b (e.g., the medial or distal 12 side) of the second bone 114. In this way, no through or bore hole is required to be made in the second side 114b of the second bone 114.

The flexible segment 116 can be manufactured out of a variety of fibers or filaments including but not limited to polymer filaments (e.g. HMWPE, UHMWPE, PET, PTFE, PEEK, PEKK, PLA, PLLA, etc.), metallic filaments (e.g. Nitinol, Titanium, Titanium alloys, Tantalum, Stainless Steel, etc.), or organic filaments (e.g. Collagen, Silk, etc.), or other filaments such as carbon fiber or carbon nanotubes, etc., and can be made of resorbable and/or biologic materials. Flexible segment 116 can include, but is not limited to, a coreless suture, a suture with a jacket and a central core, a tape, or any other tension member available or contemplated, can be poly-coated or uncoated, and can include collagen. Flexible segment 116, which can include one or more suture threads 208 (FIGS. 2A-2B), can extend between the distal end 104b of the first anchor 104 and the proximal end 110a of the second anchor 110 to adjust the distance L1 between the first and second bones 108, 114. Additionally, the flexible segment 116 can extend beyond the distal end 104b of the first anchor 104 (e.g., suture threads 208 can be manipulated proximally to the first bone 108), and/or beyond the proximal end 110a of the second anchor 110 (e.g., the suture threads 208 may extend through the second anchor 110 toward its distal tip 202 (FIGS. 2A-2B)), as further described below. Further, the flexible segment 116 can extend beyond the proximal end 104a of first anchor 104, and through an opening 104c of first anchor 104, as further discussed below.

Figure 2A:
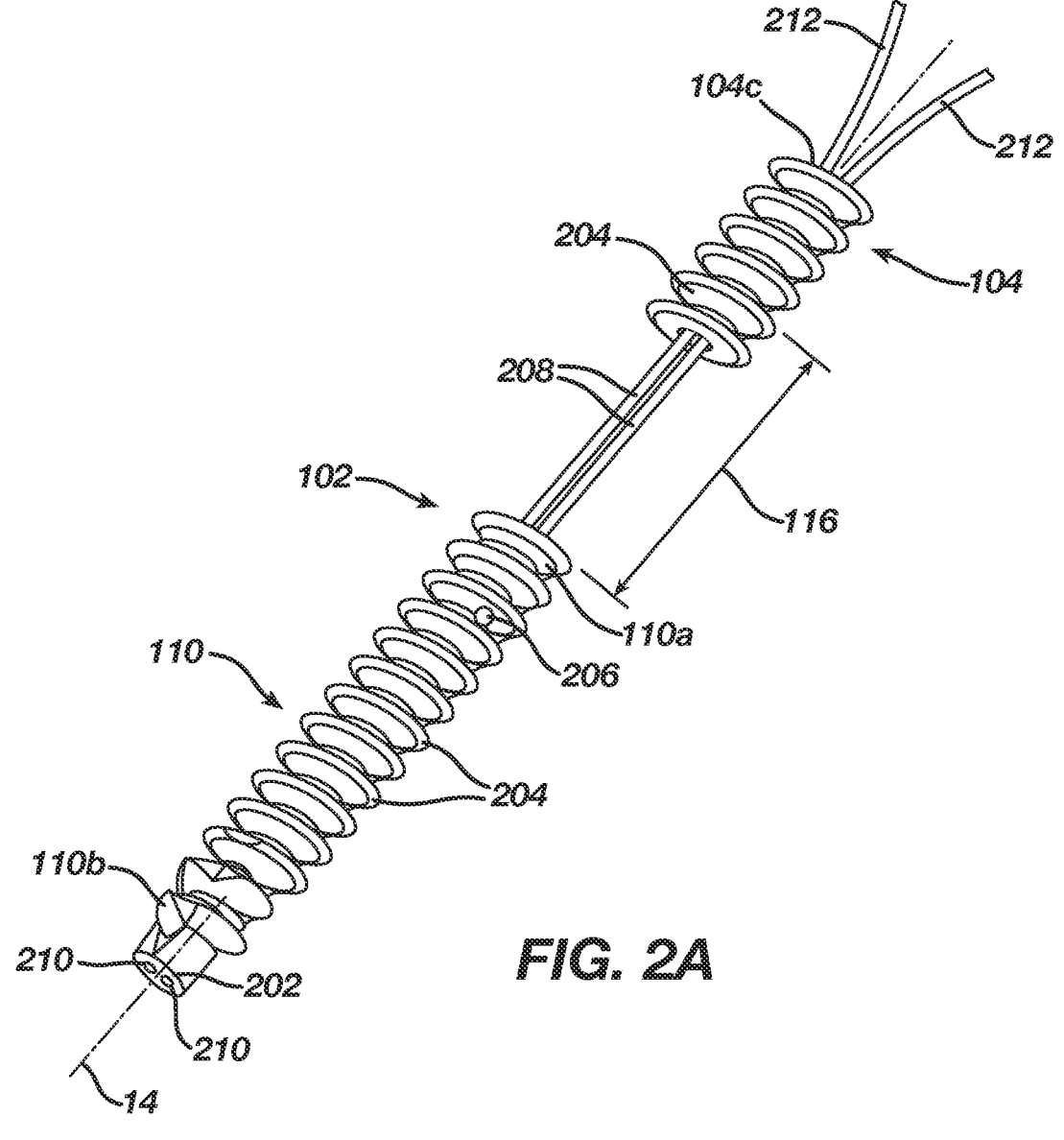
FIG. 2A is a perspective view of an example apparatus used for lateral fixation syndesmosis repair between two bones according to aspects of the present invention.
Figure 2B:
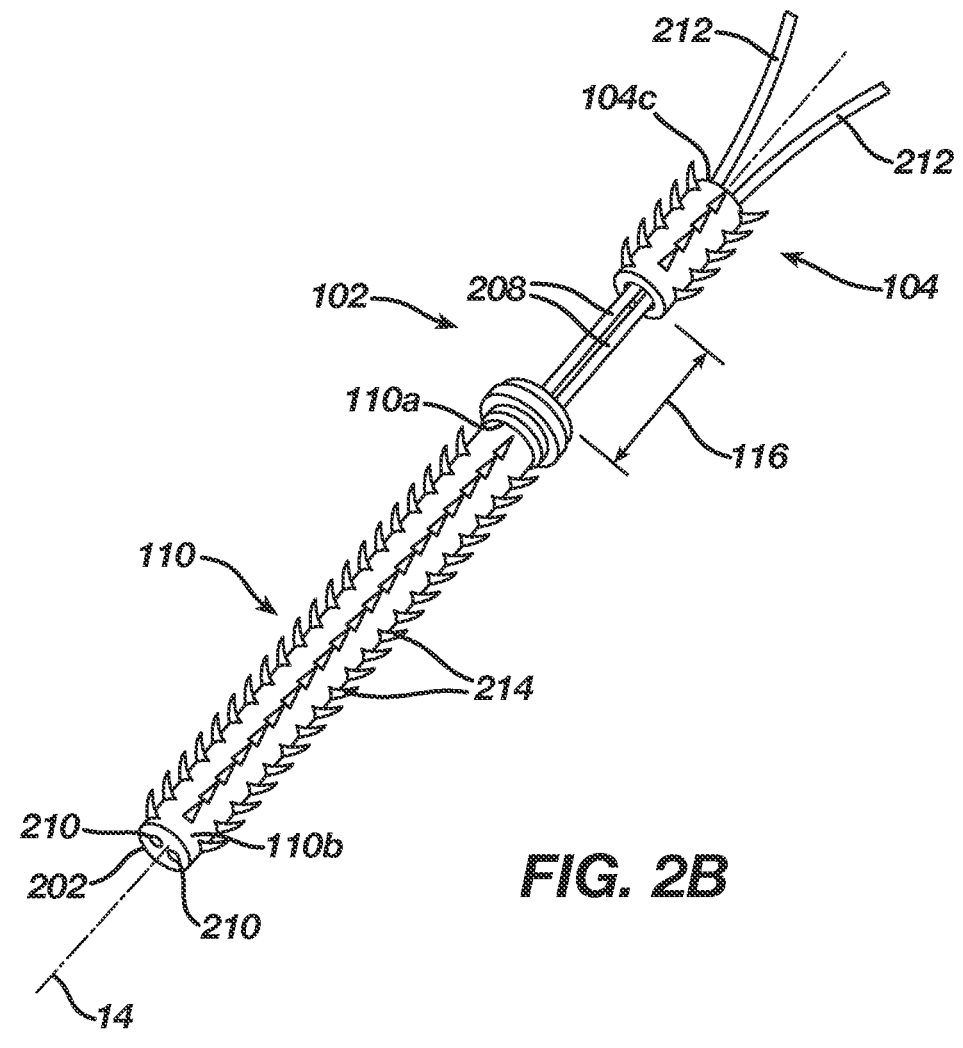
FIG. 2B is a perspective view of an example apparatus used for lateral fixation syndesmosis repair between two bones according to aspects of the present invention.
Figure 3:
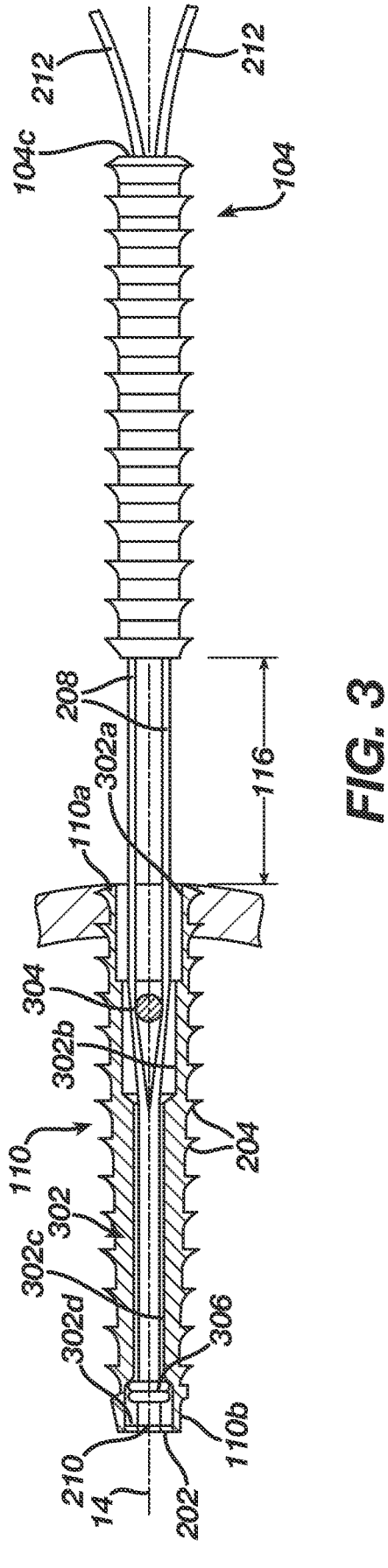
FIG. 3 is a cross-sectional view of the example apparatus of FIG. 2A as installed in a tibia and fibula according to aspects of the present invention.

FIGS. 2A-2B and 3 illustrate examples of an apparatus 102 used to provide lateral fixation syndesmosis repair of the tibia and fibula bones. The second anchor 110 may include a rigid elongate member including proximal end 110a and distal end 110b configured for insertion into the second bone 114 and terminating at a distal tip 202. The second anchor 110 can further include one or more external threads 204 (FIG. 2A) or one or more barbed ribs 214 (FIG. 2B) extending at least partially between the proximal and distal ends 110a, 110b. A second anchor 110 including external threads 204 (FIG. 2A) can be inserted into the second bone 114 via screwing or threading, as further described below. Alternatively, a second anchor 110 including barbed ribs 214 (FIG. 2B) can be inserted into the second bone 114 via pushing. That is, similar to a standard push-in rivet, barbed ribs 214 may be flexible and configured such that when second anchor 110 is pushed into second bone 114, barbed ribs 214 can deflect and then spring back to lock second anchor 110 securely in place within the second bone 114. One skilled in the pertinent art will appreciate that, aside from the disclosed examples, the second anchor 110 may include any style of bone anchor (e.g., barbed, threaded, screw-in, expanding, interference fit, etc.).

The first anchor 104 may include a rigid elongate member including proximal end 104a and distal end 104b configured for insertion into the first bone 108. Similar to a second anchor 110 including external threads 204 (FIG. 2A), first anchor 104 can also include external threads 204. Alternatively, similar to a second anchor 110 including barbed ribs 214 (FIG. 2B), first anchor 104 can also include barbed ribs 214. As further discussed herein, first anchor 104 may include an opening 104c such that flexible segment 116 may be run through the first anchor 104, and one or more proximal ends 212 of suture threads 208 of flexible segment 116 may be received through the opening 104c. The proximal ends 212 may then be adjusted, for example, pulled or loosened, to adjust the length of flexible segment 116 and thereby the distance L1 between the first and second bones 108, 114, as discussed herein.

As particularly shown in FIG. 3, the second anchor 110 can further include a bore 302 extending from the proximal end 110a at least partially towards the distal end 110b, generally along a longitudinal axis 14 of the apparatus 102. The bore 302 can include a proximal region 302a, an intermediate region 302b distal to the proximate region 302a including a first support structure 304 therein, and a distal region 302c extending from the intermediate region 302b to a recess 302d in the distal tip 202. The intermediate region 302b and distal region 302c may have a circular or other desired cross-sectional shape, with the distal region 302c having a diameter or other maximum cross-section smaller than the intermediate region 302b. The recess 302d may have a diameter or other cross-section larger than the distal region 302c, which can be shaped or otherwise configured to receive a knot 306 or otherwise fix distal ends 210 (e.g., a crimp eyelet pin, etc.) of suture threads 208 of the flexible segment 116, as described elsewhere herein.

A first support structure 304 may be provided within the bore 302, e.g., across the intermediate region 302b substantially perpendicular to the longitudinal axis 14. In one example apparatus, holes 206 (FIG. 2A) may be provided through opposite side walls of the second anchor 110 into the intermediate region 302b and a first support structure 304, e.g., a pin, may be inserted into the holes 206 such that the first support structure 304 extends across the intermediate region 302b and substantially permanently attached thereto, e.g., by one or more of press-fit or other interference fit, bonding with adhesive, sonic welding, soldering, and the like. In an alternative example apparatus, the holes 206 may be omitted and a first support structure 304 may be inserted through the intermediate region 302b and positioned and fixed across the intermediate region 302b, e.g., by one or more of interference fit, bonding with adhesive, sonic welding, soldering, and the like. In another example apparatus, a support structure may be integrally formed with the second anchor 110, e.g., machined, cast, molded, and the like from the same piece of material as the rest of the second anchor 110. The pin or other first support structure 304 generally has a diameter or other cross-section smaller than the intermediate region 302b such that the flexible segment 116 may be wrapped at least partially around the first support structure 304, as described further elsewhere herein.

The external threads 204 of first anchor 104 and/or second anchor 110 (FIG. 2A) may extend from the respective proximal end 104a, 110a helically towards the respective distal end 104b, 110b. With respect to second anchor 110, for example, the external threads 204 may extend entirely to the distal tip 202 or the external threads 204 may terminate before the distal tip 202, e.g., to provide a smooth-walled, unthreaded distal tip (not shown). With respect to the first anchor 104 and/or second anchor 110, the external threads 204 may have a substantially uniform configuration along the threaded region, or the external threads 204 may be varied as desired, e.g., having different heights, edges, and/or axial spacing (threads per millimeter), as desired.

Similar to external threads 204 (FIG. 2A), the barbed ribs 214 of first anchor 104 and/or second anchor 110 (FIG. 2B) may extend from the respective proximal end 104a, 110a towards the respective distal end 104b, 110b, and in a repeating distally downward angled pattern. With respect to second anchor 110, for example, the barbed ribs 214 may extend from the proximal end 110a entirely to the distal tip 202 or the barbed ribs 214 may terminate before the distal tip 202, e.g., to provide a smooth-walled distal tip (not shown). The barbed ribs 214 may have a substantially uniform configuration along the barbed region, or the barbed ribs 214 may be varied as desired, e.g., having different lengths, angles, and/or spacing (barbs per millimeter), as desired.

Optionally, the external threads 204 (or barbed ribs 214) of second anchor 110 may end before the proximal-most edge of the second anchor 110, e.g., about half to one millimeter (0.5-1.0 mm). Such an offset may facilitate identifying the end of the second anchor 110, e.g., to identify the interface between the second anchor 110 and the driver tool 50 during delivery of the second anchor 110 into the second bone 114, as further discussed below. In addition, the offset may provide an unthreaded (or un-barbed) region on the proximal end 110a in case the second anchor 110 extends a small distance from a bone into which it is implanted, which may reduce risk of irritation and/or damage to adjacent tissue.

The flexible segment 116 may be an elongate length of suture or other filament having one or more distal ends 210. During assembly, the distal ends 210 may be directed into the bore 302 of the second anchor 110, e.g., through the proximal region 302a, into the intermediate region 302b, wrapped at least partially around the first support structure 304, and then into the distal region 302c until the distal ends 210 exit the bore 302 at the distal tip 202. The distal ends 210 may then be secured together (e.g., by tying one or more knots 306, attaching a crimp eyelet pin, etc.), seated within the recess 302d, that have a cross-section larger than the distal region 302c, thereby preventing the distal ends 210 from being pulled back through the bore 302 during implantation. Alternatively, the distal ends 210 may be directed through the bore 302 from the distal tip 202, wrapping the ends 210 at least partially around the first support structure 304, and exiting the proximal region 302a before tying the knot 306 within the recess 302d. In either of the above-described methods of assembly, one or more proximal ends 212 of suture threads 208 of flexible segment 116 (FIGS. 2A-2B) can be received through the first anchor 104, as further described below.

Figure 4:
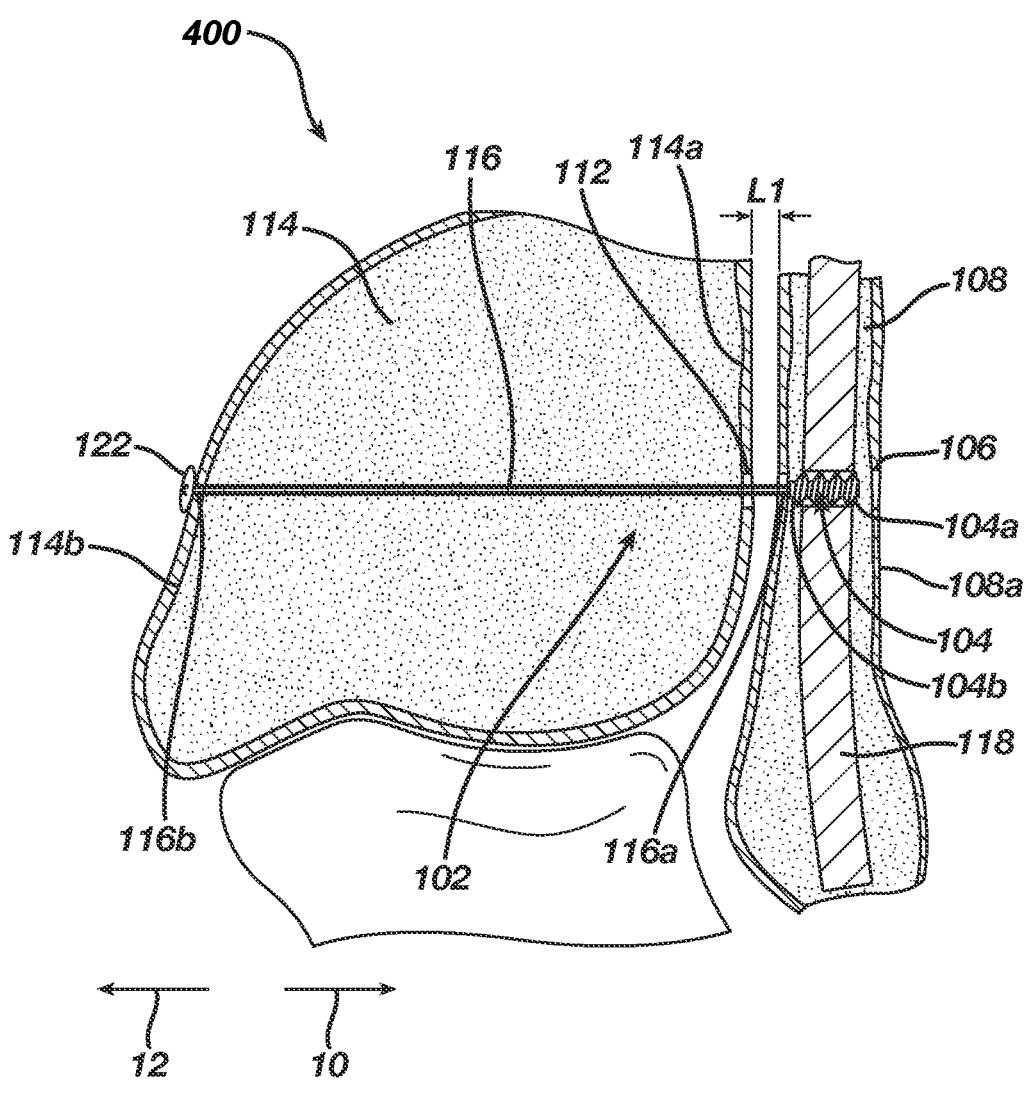
FIG. 4 is an illustration of an example system for lateral fixation syndesmosis repair according to aspects of the present invention.

FIG. 4 is an illustration of another example system 400 for lateral fixation syndesmosis repair. System 400 of FIG. 4 may be similar to system 100 of FIG. 1, except that flexible segment 116 of system 400 may extend from the distal end 104b (and/or beyond the proximal end 104a of first anchor 104, as discussed above) of first anchor 104 to a second side 114b of second bone 114. Apparatus 102 of system 400 may include a button 122 configured to engage with the second side 114b of the second bone 114 and to receive a distal end 116b of flexible segment 116. For example, the distal end 116b of flexible segment 116 may include a loop that can be wound through button 122, or may include an open end that can be, e.g., knotted or otherwise attached to button 122.

Figures 5A, 5B:
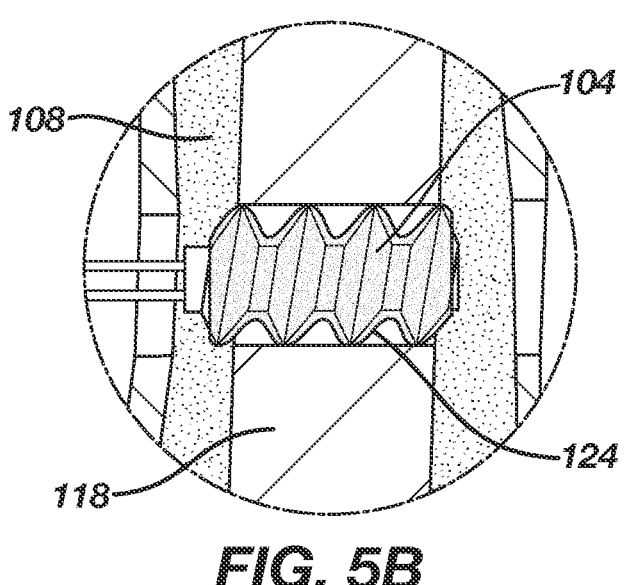
FIGS. 5A-5B are an illustration of an example system for lateral fixation syndesmosis repair according to aspects of the present invention.

FIGS. 5A-5B are an illustration of another example system 500 for lateral fixation syndesmosis repair. System 500 of FIGS. 5A-5B may be similar to system 100 of FIG. 1 and/or system 400 of FIG. 4, except that apparatus 102 of system 500 may include a sleeve 124 configured for insertion into a non-threaded bore hole 118a of nail 118, as discussed above. First anchor 104 may be configured for insertion into the sleeve 124, as particularly shown in FIG. 5B, followed by insertion into the non-threaded bore hole 118a. A benefit of the sleeve 124 is that it allows for the indirect engagement of the first anchor 104 with the nail 118, even when first anchor 104 may not be configured to directly engage (e.g., via threading, screwing, etc.) with nail 118.

FIG. 6 is an illustration of a nail 118 that may be used in a system for lateral fixation syndesmosis repair, such as system 100, 400, and/or 500. As discussed herein, a nail 118 may be implanted approximately vertically within the first bone 108 (e.g., fibula), and fastened to the first bone 108 via one or more nail fasteners 118b. The nail 118 may include one or more bore holes 118a, such that the first anchor 104 may be inserted into and/or through the bore hole(s) 118a, and/or the second anchor 110 may be inserted through the bore hole(s) 118a (e.g., prior to being inserted into the second bone 114), as discussed herein. The use of nail 118 may prevent an unstable fibular fracture and/or decrease patient recovery time associated with a fibular fracture as first anchor 104 can engage with the nail 118 rather than the lateral side of the first bone 108.

Figure 7:
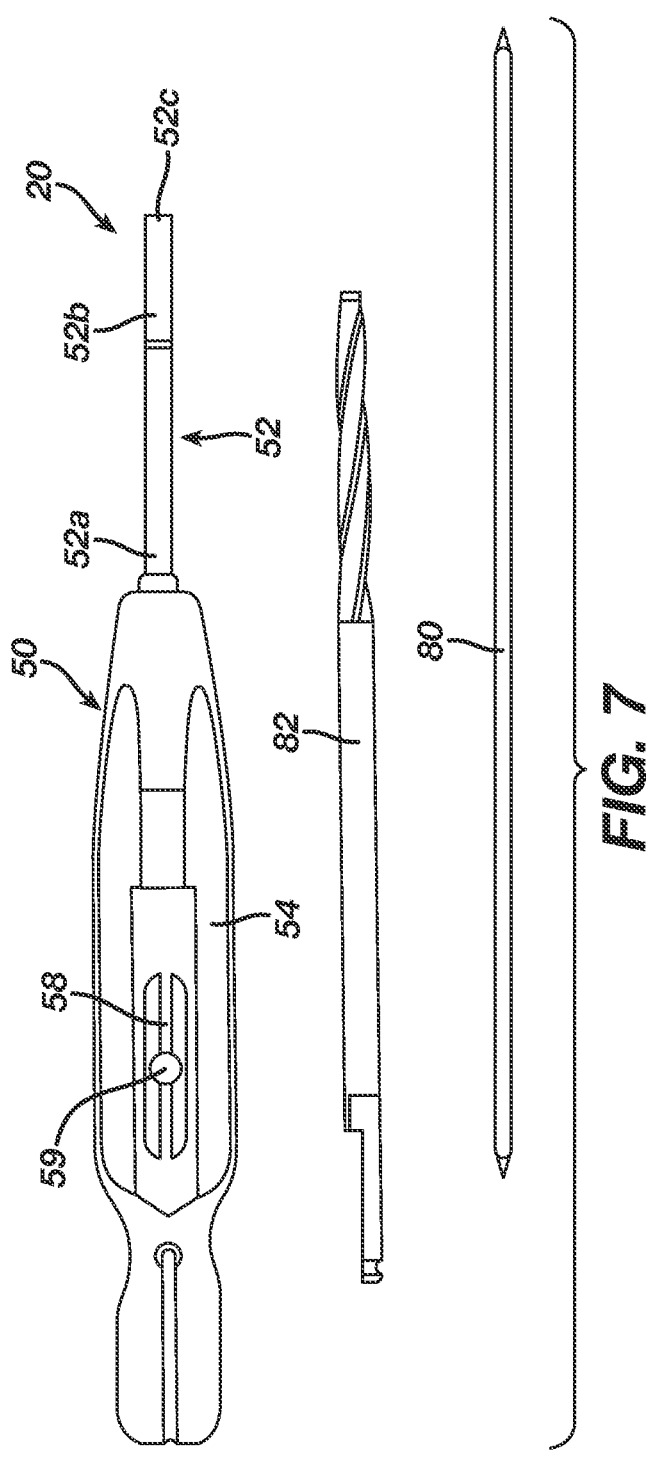
FIG. 7 shows an example of a delivery tool kit according to aspects of the present invention.

Turning to FIG. 7, an example of an entire kit is shown that may be included in a system 20 for performing a procedure including implantation of an apparatus 102, such as that shown in FIG. 2A. As shown, the kit generally includes a Kirschner wire 80, a custom drill 82 for site preparation, and the driver tool 50, which houses many of the other components during the early phases of installation. Optionally, the second anchor 110 may be preloaded into the driver tool 50, as further discussed below.

The driver tool 50 generally includes an elongate tubular outer shaft 52 including a proximal end 52a having a handle 54 thereon, a distal end 52b terminating in a distal tip 52c, and a lumen (not shown) extending between the proximal and distal ends 52a, 52b. Optionally, the handle 54 includes one or more additional features, e.g., a cleating structure 58 and an actuator 59 for releasably securing the suture threads 208 of flexible segment 116 used to secure the second anchor 110 to the driver tool 50, as described elsewhere herein.

FIGS. 8-13 provide an example method for installing the apparatus 102, such as that shown in FIG. 2A, between a first bone 108, e.g., the fibula, and a second bone 114, e.g., the tibia, using the system 20 shown in FIG. 7, to provide lateral fixation syndesmosis repair of the bones relative to one another, e.g., to treat a syndesmotic injury. It will be appreciated that the apparatus, systems, and methods described herein may also be used in other locations and/or procedures, e.g., to provide approximation between two bones other than the tibia and fibula.

Figure 8:
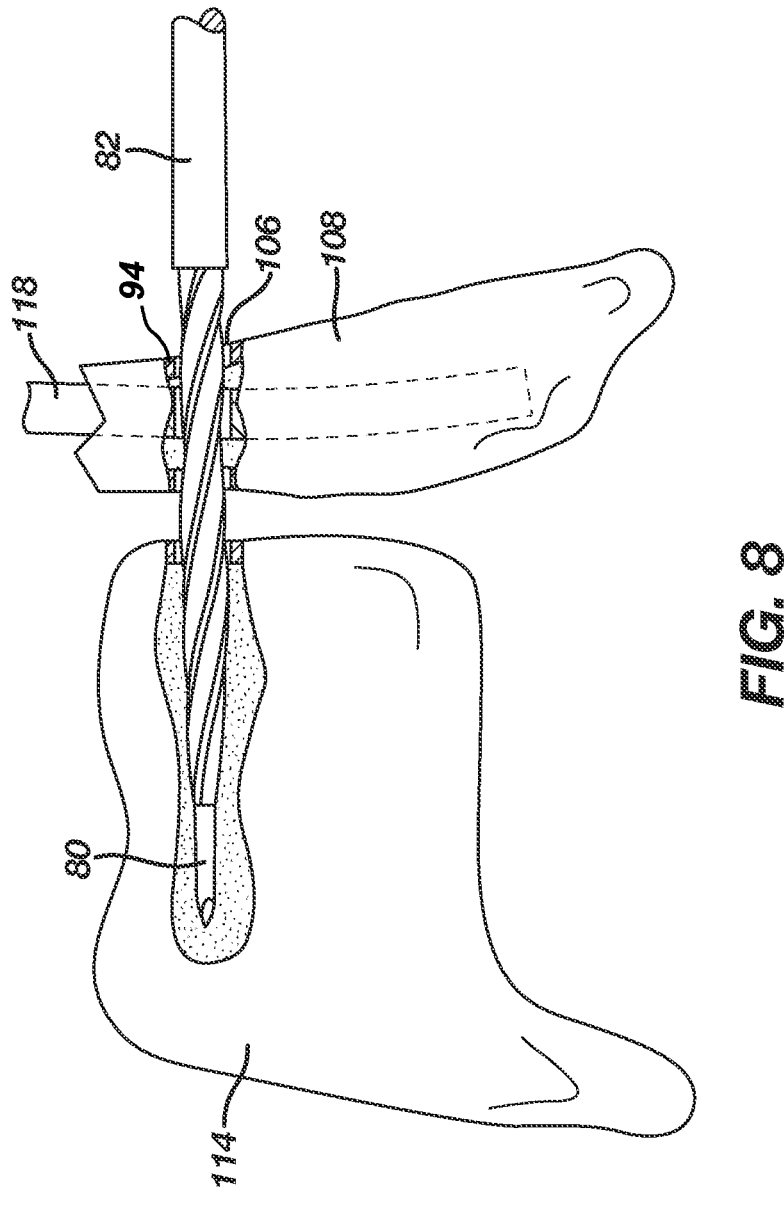
FIG. 8 is a cross-sectional view of a tibia and fibula showing an example step of an example method for installing an apparatus, such as that shown in FIG. 2A.

Initially, as shown in FIG. 8, the Kirschner wire 80 may be placed through the first bone 108, including through a bore hole 118a of nail 118, and into the second bone 114 at the appropriate location, e.g., using conventional methods, and then a drill 82 may be introduced over the Kirschner wire 80 to create the first hole 106 through the first bone 108 and bore hole 118*a* of nail 118, and at least partially into the second bone 114. In the example kit shown in FIG. 7, the drill 82 may use a custom drill bit 82 sized to create a clearance hole 94 larger than four millimeters (4.0 mm), e.g., about 4.1 mm, to accommodate a second anchor 110 having an outer thread diameter of four millimeters (4.0 mm). It will be appreciated that other sizes may be provided, as desired.

Figure 9:
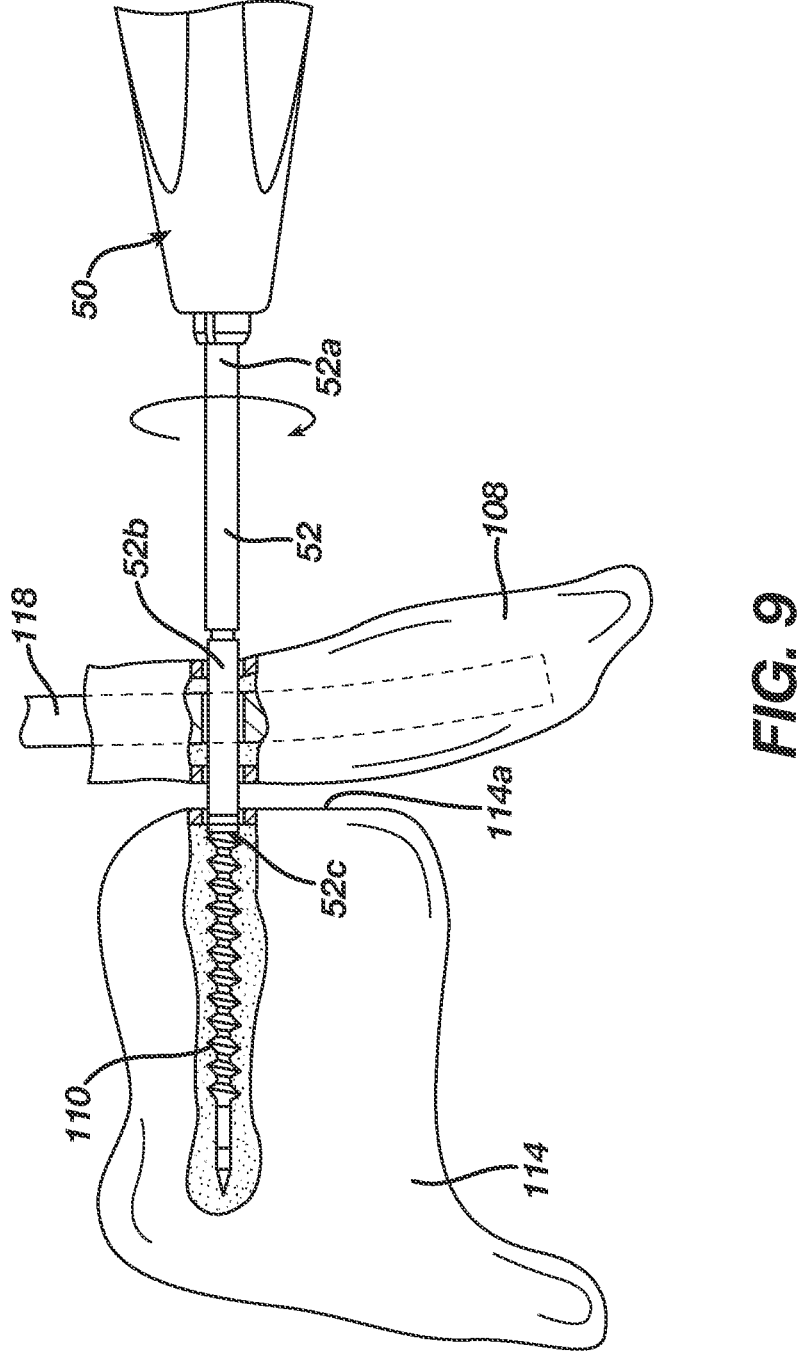
FIG. 9 is a cross-sectional view of a tibia and fibula showing an example step of an example method for installing an apparatus, such as that shown in FIG. 2A.

Turning to FIG. 9, the second anchor 110 may then be introduced through the clearance hole 94, through the bore hole 118*a* (FIG. 6) of nail 118, and threaded (or pushed if using second anchor 110 as in FIG. 2B) into the second bone 114 to a desired depth. For example, the second anchor 110 may be secured to the distal end 52*b* of the outer shaft 52 of the driver tool 50. Once the distal tip 202 of the second anchor 110 engages the second bone 114, the driver tool 50 may be rotated and advanced to thread the second anchor 110 into the second bone 114 to a desired depth, e.g., such that the proximal end 110*a* of the second anchor 110 is substantially flush with the first side 114*a* of the second bone 114. As can be seen, the clearance hole 94 (FIG. 8) drilled through the first bone 108 and the bore hole 118*a* of nail 118 have sufficient size to accommodate the outer shaft 52 of the first anchor driver tool 50 passing therethrough to thread the second anchor 110 into the second bone 114.

Figure 10:
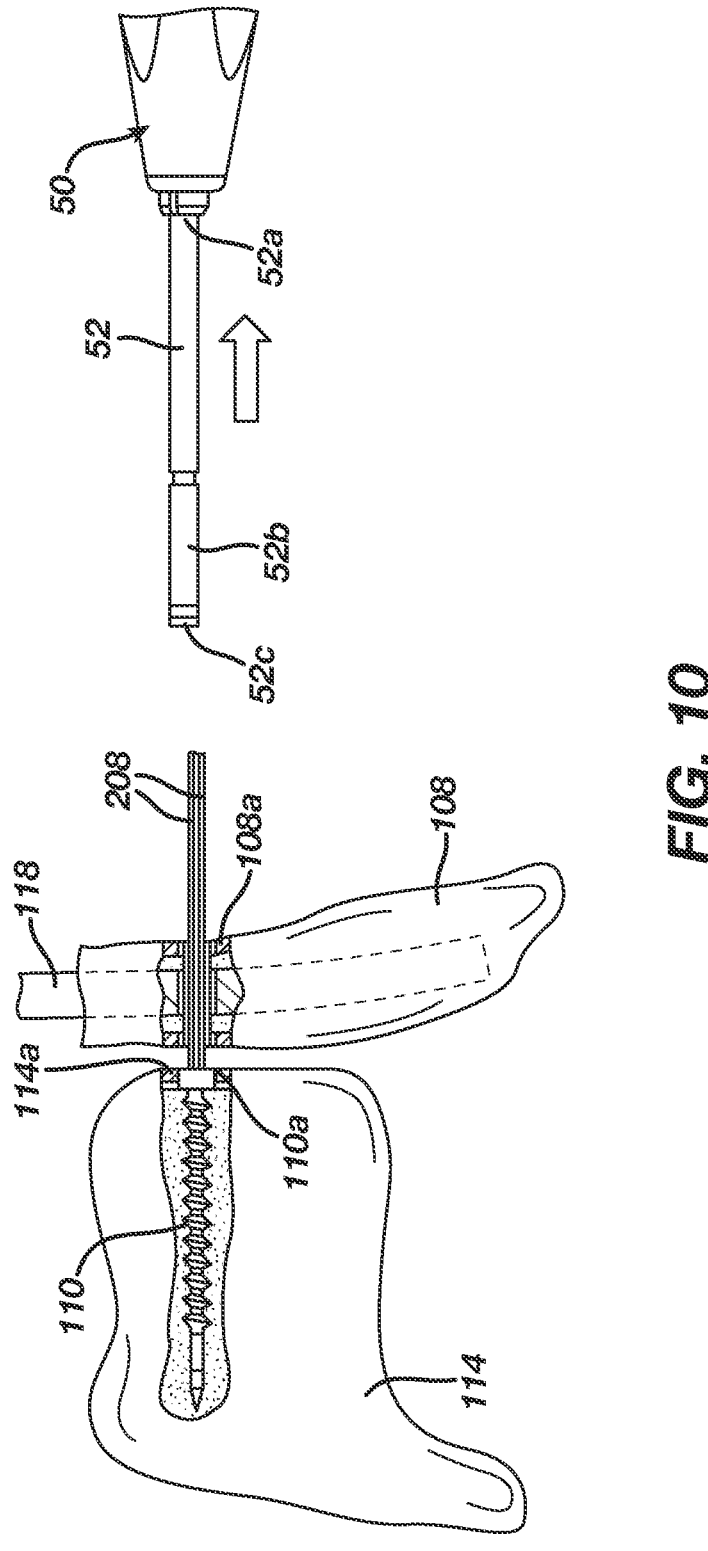
FIG. 10 is a cross-sectional view of a tibia and fibula showing an example step of an example method for installing an apparatus, such as that shown in FIG. 2A.

Turning to FIG. 10, once the second anchor 110 is threaded (or otherwise secured) into the second bone 114 to the desired depth, the driver tool 50 may be removed. Since the second anchor 110 is secured to the outer shaft 52, the user first releases the second anchor 110 from the driver tool 50, e.g., by releasing the suture threads 208 of the flexible segment 116 from the cleat 58, and then the driver tool 50 may be withdrawn. As the driver tool 50 is withdrawn, the proximal ends 212 of the suture threads 208 of the flexible segment 216 may slide through the lumen of the driver tool 50 and hang freely out the first side 108*a* of the first bone 108.

Figure 11:
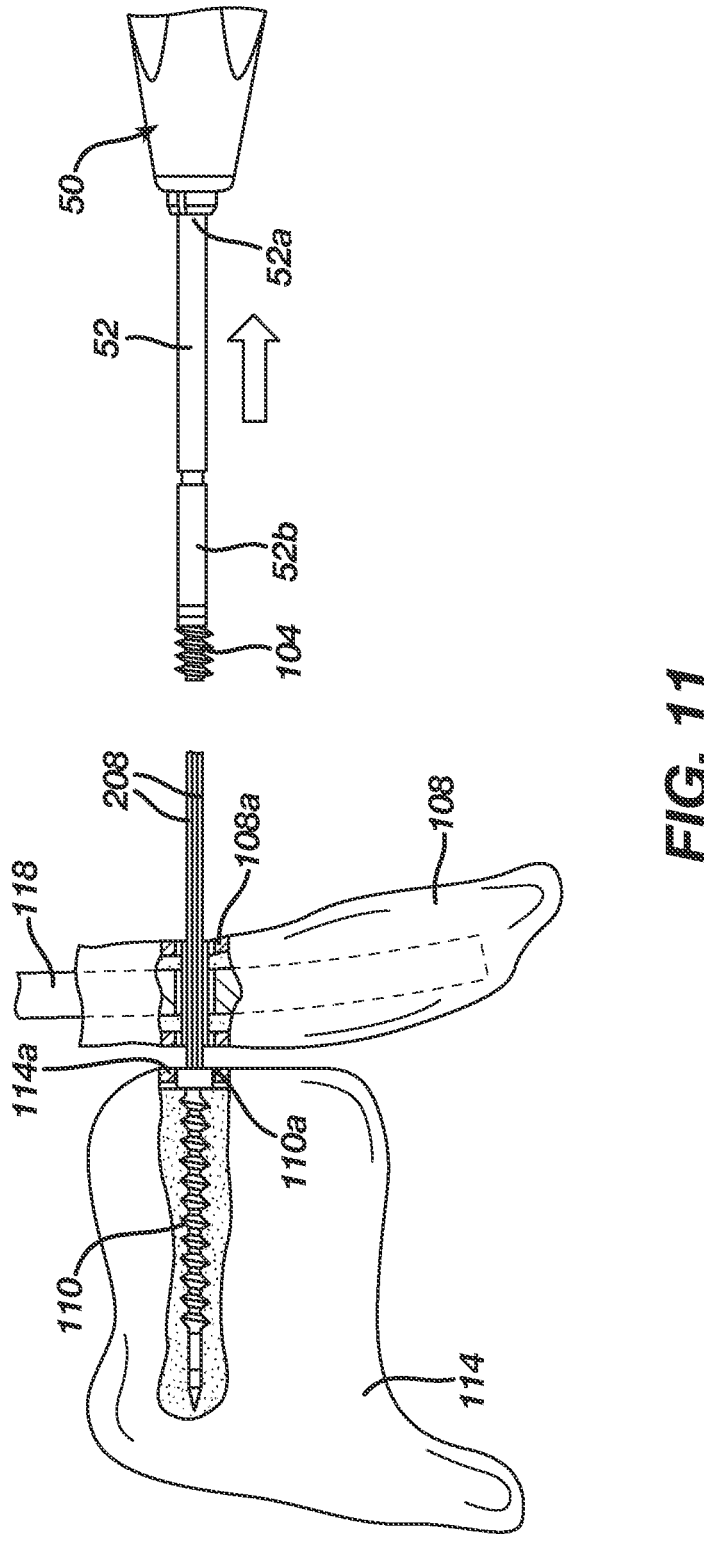
FIG. 11 is a cross-sectional view of a tibia and fibula showing an example step of an example method for installing an apparatus, such as that shown in FIG. 2A.
Figure 12:
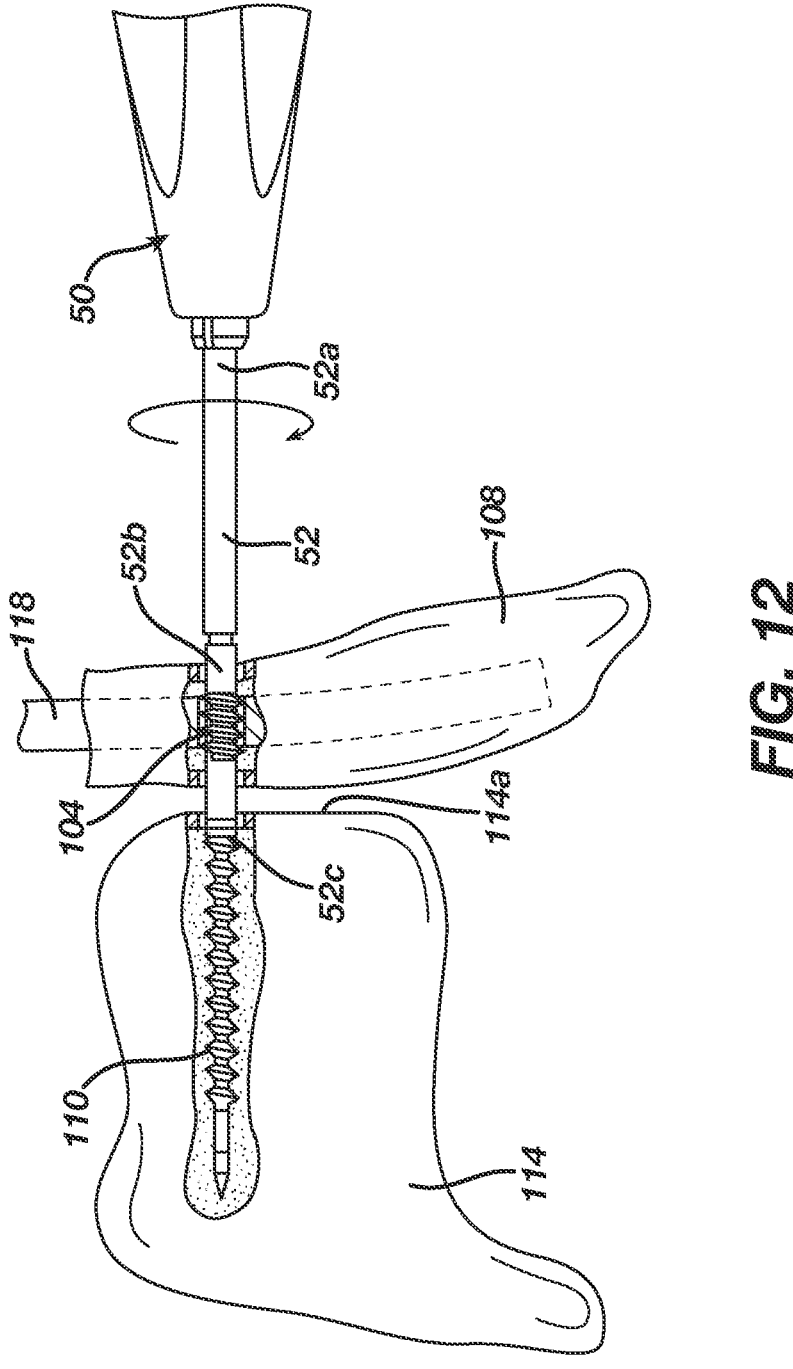
FIG. 12 is a cross-sectional view of a tibia and fibula showing an example step of an example method for installing an apparatus, such as that shown in FIG. 2A.

Turning to FIGS. 11-12, once the driver tool 50 has been removed, and proximal ends 212 of the suture threads 208 are hanging freely out the first side 108*a* of the first bone 108 (FIG. 11), the proximal ends 212 (FIG. 3) can be slid through the first anchor 104 (e.g., through opening 104*c*, FIG. 3). The driver tool 50 can be engaged to the first anchor 104 and rotated or otherwise advanced to insert (e.g., thread or slide, depending on whether bore hole 118*a* is threaded or non-threaded, as discussed herein) the first anchor 104 into the first bone 108 (FIG. 12).

Figure 13:
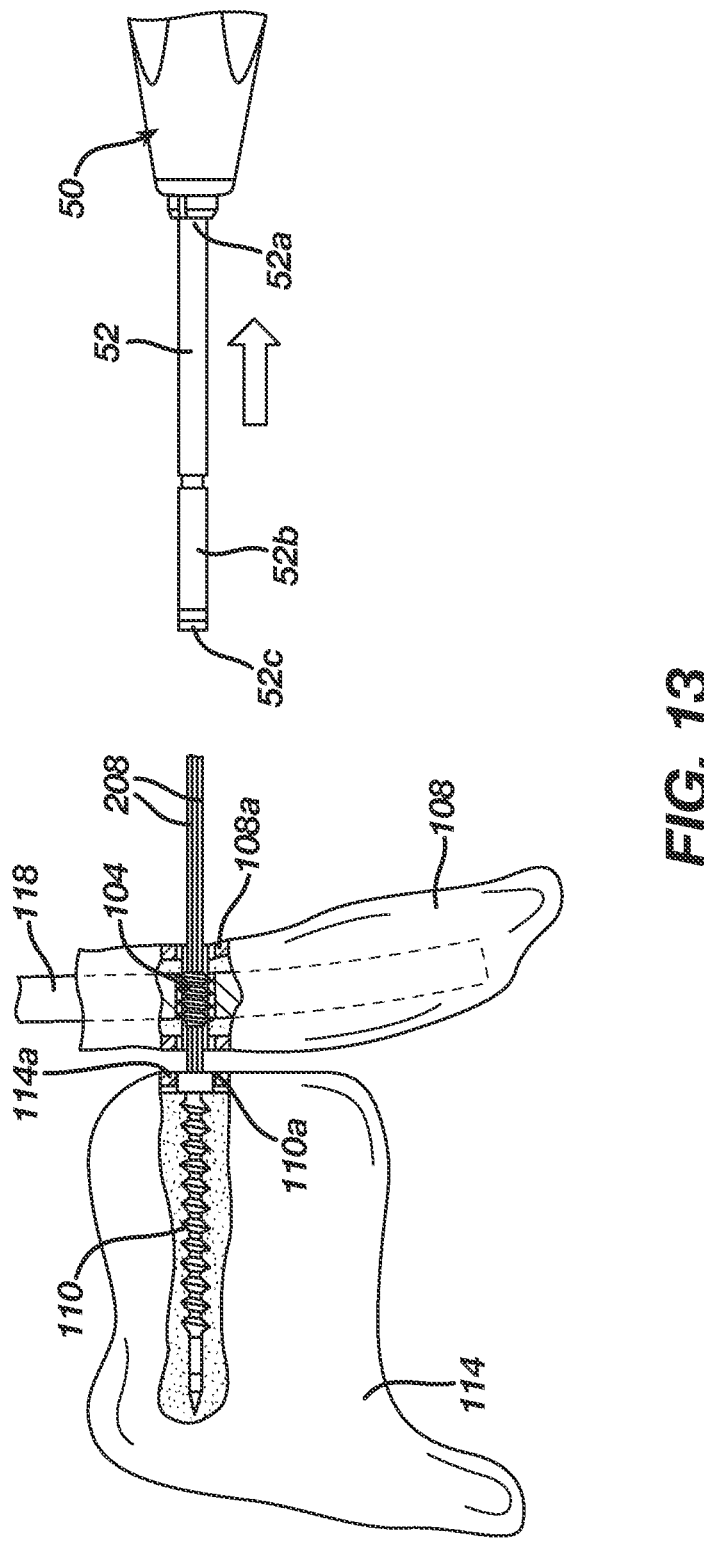
FIG. 13 is a cross-sectional view of a tibia and fibula showing an example step of an example method for installing an apparatus, such as that shown in FIG. 2A.

Once the proximal ends 212 (FIG. 3) have been received through the opening 104*c* of first anchor 104, as shown in FIG. 13, the proximal ends 212 can be manipulated (e.g., tightened, loosened, etc.), as described herein, to adjust the length of flexible segment 116 to a desired length, thereby fixing the distance between the first and second bones 108, 114.

The descriptions contained herein are examples of embodiments of the invention and are not intended in any way to limit the scope of the invention. As described herein, the invention contemplates many variations and modifications of structures and methods, including alternative materials, alternative configurations of component parts, and alternative method steps. Modifications and variations apparent to those having skill in the pertinent art according to the teachings of this disclosure are intended to be within the scope of the claims which follow.

What is claimed is:

1. An apparatus approximating of two bones, comprising:
a nail disposed within a first bone; and
a first anchor comprising a proximal end and a distal end and configured to be inserted into a first hole in the first bone, wherein the proximal end is configured to interface with the nail such that there is a first distance between the proximal end and the lateral side of the first bone and the distal end is configured to interface with the nail such that there is a second distance between the distal end and the medial side of the first bone,
wherein the first anchor comprises a threaded outer surface, and
wherein one or more of the proximal end and the distal end of the first anchor is configured to engage with the first bone via the threaded outer surface.

2. The apparatus of claim 1, wherein the proximal end of the first anchor is configured to lay countersunk to the first bone.

3. The apparatus of claim 1, further comprising:
a second anchor configured to fixate to a second bone; and
a flexible segment extending between the first anchor and the second anchor and configured to adjust a third distance between the first and second bones.

4. The apparatus of claim 3, wherein the second anchor comprises:
a proximal end; and
a distal end configured to be inserted into a second hole in the second bone.

5. The apparatus of claim 4, wherein the second anchor passes through the first hole and is inserted within the second bone in the second hole from the distal end to the proximal end.

6. The apparatus of claim 5, wherein the second hole is disposed on a first side of the second bone, and wherein the second anchor is configured such that there is a fourth distance between the distal end of the second anchor and a second side of the second bone.

7. The apparatus of claim 3, wherein the flexible segment extends at least one of between or beyond the distal end of the second anchor and the proximal end of the first anchor.

8. The apparatus of claim 3, wherein the second anchor comprises a button configured to engage with a second side of the second bone and to receive a distal end of the flexible segment.

9. The apparatus of claim 3, wherein:
the first anchor comprises at least one opening configured to receive one or more proximal ends of the flexible segment, and
the flexible segment is configured to adjust the third distance between the first and second bones when the proximal ends are pulled in a proximal direction through the at least one opening.

10. The apparatus of claim 3, wherein the first anchor comprises at least one opening configured to receive one or more proximal ends of the flexible segment.

11. The apparatus of claim 10, wherein the flexible segment is configured to adjust the third distance between the first and second bones when the proximal ends are pulled in a proximal direction through the at least one opening.

12. The apparatus of claim 1, further comprising a cap configured to engage with the proximal end of the first anchor and to lay flush with or countersunk to the lateral side of the first bone.

13. A method approximating of two bones, the method comprising:
fixating a nail within a first bone; and
fixating a first anchor to the first bone,
wherein the first anchor comprises a proximal end, a distal end, and a threaded outer surface, wherein the first anchor is configured to be inserted into a first hole in the first bone, wherein the proximal end of the first anchor is configured to interface with the nail such that there is a first distance between the proximal end and the lateral side of the first bone, and wherein the distal end of the first anchor is configured to interface with the nail such that there is a second distance between the distal end and the medial side of the first bone, and wherein one or more of the proximal end and the distal end of the first anchor is configured to engage with the first bone via the threaded outer surface.

14. The method of claim 13, further comprising:

fixating a second anchor to a second bone; and fixating a flexible segment between the first anchor and the second anchor, wherein the flexible segment is configured to adjust a third distance between the first and second bones.

15. The method of claim 13, wherein the nail comprises a non-threaded bore hole, the method further comprising:

fixating a sleeve into the non-threaded bore hole of the nail, wherein fixating the first anchor to the first bone comprises inserting the distal end of the first anchor into the non-threaded bore hole of the nail and fixating the first anchor into the sleeve.

16. The method of claim 13, wherein the nail comprises a non-threaded bore hole, and wherein fixating the first anchor to the first bone comprises inserting the distal end of the first anchor into the non-threaded bore hole of the nail, the method further comprising:

fixating a cap to the proximal end of the first anchor, the cap configured to lay flush with or countersunk to the lateral side of the first bone.

17. The apparatus of claim 1, wherein the first anchor is free from engagement with the lateral side of the first bone.

18. The apparatus of claim 1, wherein an outer diameter of the first anchor remains consistent across the length of the first anchor.

19. The apparatus of claim 1, wherein the first anchor extends the full width of the nail.

\* \* \* \* \*